United States Patent [19]
Ulrich et al.

[11] Patent Number: 5,691,379
[45] Date of Patent: Nov. 25, 1997

[54] DIHYDROLIPOIC ACID AS AN OPHTHALMOLOGICAL AGENT TO SUPPRESS INTOLERANCE REACTIONS IN THE AREA BETWEEN IMPLANTS AND LIVING BODY TISSUE

[75] Inventors: Heinz Ulrich, Niedernberg; Erich Franz Elstner, Grobenzell, both of Germany

[73] Assignee: ASTA Medica Aktiengesellschaft, Dresden, Germany

[21] Appl. No.: 557,187

[22] PCT Filed: Apr. 11, 1994

[86] PCT No.: PCT/EP94/01110

§ 371 Date: Mar. 15, 1996

§ 102(e) Date: Mar. 15, 1996

[87] PCT Pub. No.: WO94/27592

PCT Pub. Date: Dec. 8, 1994

[30] Foreign Application Priority Data

May 22, 1993 [DE] Germany ............... 43 17 173.7

[51] Int. Cl.⁶ ................ A61K 31/19; A61K 31/385
[52] U.S. Cl. ............... 514/557; 514/27; 514/456; 514/440
[58] Field of Search ............ 514/27, 456, 557, 514/440

[56] References Cited

PUBLICATIONS

Seis, et al: "Antioxidant Functions of Vitamins", Ann. N.Y. Acad. Sci. vol. 669, 30 Sep. 1992, pp. 7–20, see p. 16, see p. 17–fig 6; see p. 18, line 4–7, line 15–20.

Kagan, et al: "Dihydrolipoic Acid—A Universal antioxidant both in the Membrane and in the Aqueous Phase", Biochem. Pharmacol. vol. 44, No. 8, 20 Oct. 1992, pp. 1637–1649, see abstract.

Prehn et al: "Dihydrolipoate Reduces Neuronal Injury After Cerebral Ischemia", J. Cereb.Blood Flow Metab., vol. 12, No. 1, Jan. 1992, pp. 78–87, see abstract.

Freialeben et al: "Free–radical Scavenging Activities, Interactions and Recycling of Antioxidants", Biochem. Soc. Trans., vol. 21, No. 2, May 1993, pp. 325–330, see p. 329.

Burkart, et al: "Dihydrolipoic acid Protects Pancreatic Islet Cells from Inflammatory Attach", Agents Actions, vol. 38, No. 1–2, Jan. 1993, pp. 60–65, see abstract.

Tsuchiya, et al: "Superoxide Formed from Cigarette Smoke Impairs Polymorphonuclear Leukocyte Active Oxygen Generation Activity", Arch.Biochem.Biophys. vol. 299, No. 1, Nov. 15, 1992, pp. 30–37, see abstract.

Suzuki, et al: "Antioxidant Activities of Dihydrolipoic acid and its Structural Homologues", Free Radiac Res. Commun., vol. 18, No. 2, 1993, pp. 115–122, see abstract.

*Primary Examiner*—Phyllis G. Spivack
*Attorney, Agent, or Firm*—Cushman Darby & Cushman, IP Group of Pillsbury Madison & Sutro LLP

[57] ABSTRACT

Pharmaceutical compositions comprising dihydrolipoic acid or physiologically acceptable salts thereof are disclosed for the treatment of eye diseases and intolerance reactions in the area between implants and endoprostheses, in particular ophthalmological implants and endoprostheses with living body tissue.

8 Claims, 1 Drawing Sheet

DIHYDROLIPOIC ACID AS AN OPHTHALMOLOGICAL AGENT TO SUPPRESS INTOLERANCE REACTIONS IN THE AREA BETWEEN IMPLANTS AND LIVING BODY TISSUE

This application claims benefit of International application PCT/EP94/011110, filed Apr. 11, 1994.

BACKGROUND OF THE INVENTION

The present invention relates to the use of dihydrolipoic acid (6,8-dimercapto-octanic acid) in diseases of the eye and in intolerance reactions of the eye with implants, such as for example vitreous body and lens replacement material. Dihydrolipoic acid may also be used in the event of intolerance reactions of other body tissues with endoprostheses and implants.

Under physiological conditions, dihydrolipoic acid, the reduced form of α-lipoic acid, is involved in the regulation of the cellular redox state. Oxidation reactions due to certain highly reactive oxygen compounds have been found to trigger various symptoms through damage to cells and tissues.

Equilibria generally tend to exist intracellularly and extracellularly between the formation of reactive oxygen species and their requirement-oriented concentration regulation due to a balanced antioxidative system. This regulation system involves low molecular compounds such as vitamin A (retinol), vitamin C (ascorbic acid), vitamin E (α-tocopherol), uric acid and glutathion as well as special enzymes with antioxidative function. If this system is weakened or chronically overloaded, it should be augmented from outside by added antioxidants to achieve continuous protection against damage.

Blockage of the coenzyme α-lipoic acid is known to lead to impaired oxidative metabolism.

DE-A-40 35 456 discloses the use of dihydrolipoic acid for combating retroviruses, in particular the HIV virus. It is also possible to use a combination with another anti-retrovirally acting substance.

DE-A-40 02 706 describes dihydrolipoic acid as having an analgesic, anti-inflammatory and cytoprotective effect.

Furthermore, the radical-capturing and reducing effect of dihydrolipoic acid is known from the report published by universimed Verlag 1993 of a symposium (The status of antioxidants in the treatment of Diabetes mellitus). Kähler et al. report that dihydrolipoic acid displays a quench effect against peroxyl and superoxide radicals in cytosol and hydrophobic domains. Packer shows in connection with oxidative protective effect that a synergistic effect exists between vitamin E and/or vitamin C and dihydrolipoic acid. On the basis of model reactions, Burkart et al. raise the question as to whether dihydrolipoic acid should be used to suppress inflammatory processes in Type I diabetes. Elstner reports that the photooxidation of crystallines occurring due to radiation can be prevented by dihydrolipoic acid.

SUMMARY OF THE INVENTION

Figure 1:
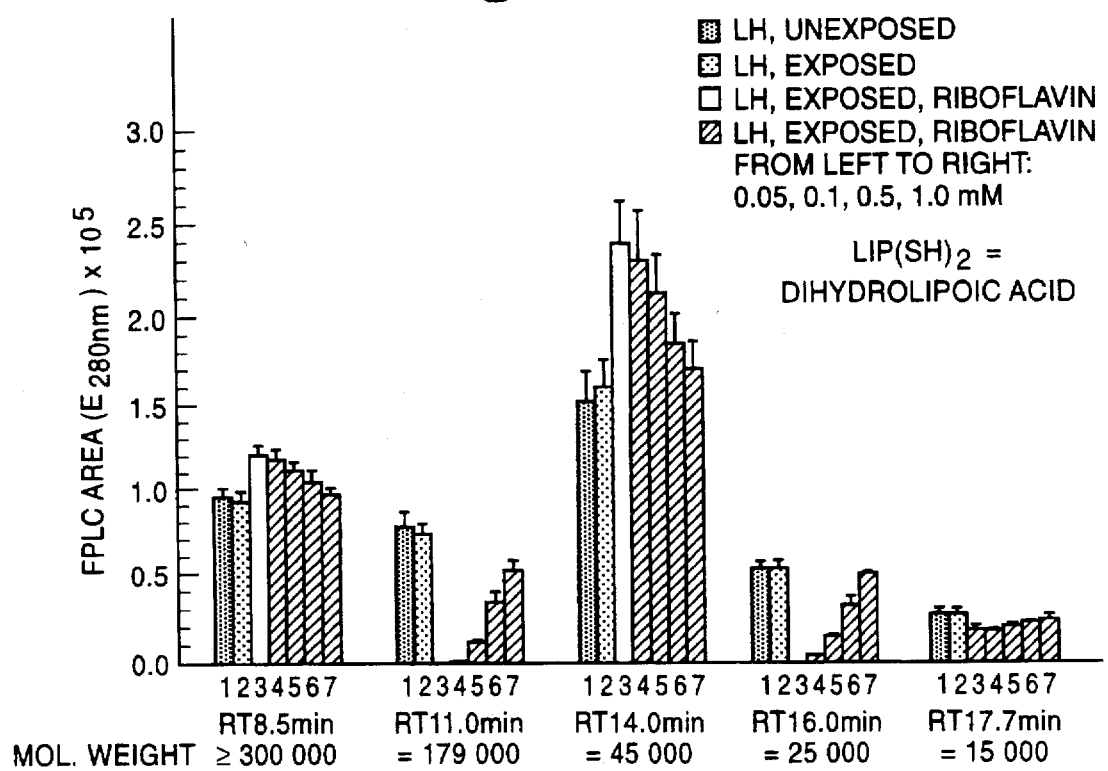
FIG. 1 shows the five main components of a lens homogenate obtained by means of FPLC filtration and the molecular weights allocated according to the retention time.

It is an object of the present invention to provide pharmaceuticals which are suitable for the treatment or prophylaxis of diseases of the eye and for the suppression and prevention of intolerance reactions in the area between implants and living body tissue.

This object is solved by using dihydrolipoic acid or its physiologically acceptable salts to prepare pharmaceutical compositions for the treatment of disorders triggered by radicals in living body tissue.

The subordinate claims describe preferred embodiments of the use according to the invention.

DETAILED DESCRIPTION OF THE INVENTION

The disorders are in particular diseases of the eye, for example cataracts, retinopathy or retrolental fibroplasia and intolerance reactions in the area between implants and endoprostheses and living body tissue. Ophthalmological implants are particularly preferred. Treatment may already be prophylactic in order in particular to avoid or reduce intolerance reactions in the area between implants or endoprostheses and living body tissue.

Dihydrolipoic acid is able to exert a favourable influence on the pathobiochemical processes caused in these disease processes by the appearance of reactive radicals.

It is possible that extensive exposure of the lens suffices to cause radiation-triggered chemical processes in which reactive, in particular oxygen-containing radicals are formed. The stress situation in the eye is very great since the lens also contains substances such as riboflavin (vitamin B) and N-formylkynurenine which, being light sensitisers, trigger radiation-related reactions. As a result thereof, discolorations and covalent protein cross-linkage occur in the lens during ageing, but intensified in the case of cataractogenesis (pathological clouding due to grey cataract). In healthy lenses the proportion of antioxidants such as ascorbate and glutathione and protecting enzymes such as glutathione peroxidase is markedly higher than in cataract lenses. Here, a higher proportion of hydrogen peroxide is also encountered. Furthermore, if a cataract is present there is also continuous oxidation of cysteine and methionine in the lens.

Similar radical-mediated protein degradations as occur in the lens tissue also occur in the vitreous body of the eye in various metabolic diseases, such as Diabetes mellitus, and also in age and on the basis of various causes, some of which are as yet unknown. In the case of premature and newly born babies exposed to elevated oxygen partial pressures in an incubator because of disturbed maturation of the lung, oxidative stress leads to the development of so-called retrolental fibroplasia.

All these processes not only change the protein structure and thus the fibrous texture of the vitreous body, and thus the light permeability thereof, but can also induce other pathological changes and thus retinopathy due to the changed traction and pressure conditions at the surrounding retina and its vessels.

The use of dihydrolipoic acid according to the invention serves for the treatment of 1. senile cataract, cataract caused by radiation, UV-radioactivity or by thermal radiation,
2. professionally caused, vitamin deficiency-induced cataract,
3. senile- or myopia-induced retinopathy,
4. retrolental fibroplasia.

The incidence of radicals may also be shown when implants and endoprostheses are inserted. These occur due to release or abrasion of minute metal or plastic species (ions or particles) which are able to induce foreign body reactions. All these processes may led to delay or disturbance or impairment of the settling process. Foreign body granulomas or projecting connective tissue may form about the implant or endoprosthesis which lead to mechanical, optical, electrical or chemical and other functional impairments, or the desired function may only be possible later or only for a limited period as a result hereof. In the case of subdermal implantation, these processes may also lead to cosmetically disturbing scar formation with subsequent shrinkage processes and impaired movement.

The release of implant material is also observed in the case of ocular implants. The inflammatory foreign body reactions induced hereby may also lead to disturbed and delayed settling as well as the formation of poorly or not at all light-permeable scar tissue in the area of the implant and thus, for example, totally or partially prevent the function thereof in maintaining or improving vision.

The foreign body reactions occurring Intra- and extracellularly thus constitute a uniform reaction of all body tissues or organs to a foreign body stimulus. It is known from various publications that only quantitative differences exist here.

The testing of the bioavailability of implants and endoprostheses, for example of ophthalmological implants, is effected in animal experiments in which the implants are introduced into the subcutaneous tissue or by intraocular implantation. It has been found that administration of dihydrolipoic acid in the form of a pharmaceutical composition during biotolerance testing is able to suppress or markedly reduce intolerance reactions. Because of the similar disturbances in the case of implants in the subcutaneous tissue, in intramuscular implantation and in intraocular implantation, use according to the invention is generally suitable for the treatment of acute diseases and also for prophylaxis in possible intolerance reactions of implants and endoprostheses.

An additional therapy possibility is thus use in vitreous body replacement (endoprostheses), anterior chamber lens replacement, endoprostheses and implants in general.

The effect of dihydrolipoic acid has been shown by investigating the consequences of UV radiation on a homogenous extract of bovine eye lenses. During this procedure the molecular weight composition and the proportion of free SH groups in the extract were determined. In photochemically triggered, degenerative processes in eye lenses the molecular weight composition changes to higher aggregates which decreases the proportion of free SH-groups which cause the cross-linkage. Radiation was carried out with and without added riboflavin and then with increasing concentration of dihydrolipoic acid.

During degranulation, activated leucocytes secrete myeloperoxidase dase into the phagosome where the myeloperoxidase reacts with $H_2O_2$ and $Cl^-$ to hypochlorous acid HOCl. This is a highly active bactericide and inactivator of numerous enzymes.

EXAMPLES

A. Exposure of extract of bovine eye lenses (lens homogenate LH) and determination of the molecular weight composition.

1. Lens homogenate of bovine eyes

Bovine eyes of freshly slaughtered animals were processed in the laboratory immediately after transport (cooled, physiological NaCl solution (0°–4° C.); duration of transport approx. 30 min.).

The lenses are isolated from bovine bulbi and intermediately stored in physiological NaCl solution after removing adhering vitreous and ciliary body residue. The drained weight of the lenses is then determined (plastic sieve). The lenses are homogenised in a mortar (on ice) precooled with a little liquid nitrogen and mixed with cooled, physiological NaCl solution in a ratio of 1 g lens per 1 ml salt solution. The mixture is then centrifuged for 30 min. at 15000 g and the aqueous supernatant that contains the water-soluble protein proportion is filtered through sterile filters (0.22 um) into brown vials with screw-top lids (20 ml). Before the vials are closed, the lens homogenate is covered with gaseous nitrogen to keep oxidation reactions due to oxygen in the air as low as possible. The lens homogenate so obtained is stored at −20° C. until used.

2. Determination of the lens homogenate-protein concentration

The Bio-Rad Protein Assay is used for quantitatively recording proteins in solutions. The assay corresponds to the method described by Bradford (1976) which is based on the shift in the absorption maximum of a phosphoric acid, methanol solution of Comassie Brilliant Blue G 250 of 465 nm to 595 nm when this dyestuff binds to protein or amino groups. Bovine serum albumin (BSA) is used as standard protein.

For the assay, 5 ml of the 1:5 diluted dyestuff reagent are mixed with 0.1 ml sample solution and the extinction is determined at 595 nm after 15 min. incubation at room temperature. 0.1 ml solvent of the protein is used as the test solution in the assay. The colour reagent is subject to ageing, particularly in dilute form. For this reason the dilution of the determining reagent is always freshly prepared and a new calibration gradient with BSA is established for each new dilution. The calibration solutions contain between 0.1 and 0.8 mg/ml BSA. The photometrically obtained extinction values are converted on the basis of the calibration curve in the form of mg protein per ml lens homogenate. The average protein content is 110–130 mg per ml lens homogenate.

3. Riboflavin-catalysed photooxidation of lens proteins

Lens homogenate is exposed together with riboflavin and then examined using FPLC (gel filtration). This reveals a change in the molecular weight composition of the lens homogenate as a function of the exposure time, high molecular weight aggregates increasingly being formed. This model reaction stimulates a possible photodynamic change in lens proteins during the cataractogenesis.

It was now investigated whether dihydrolipoic acid can influence this photodynamic damage of the lens homogenate. Dihydrolipoic acid inhibits the gel chromatographically detectable change in the lens homogenate LH due to UV radiation depending on concentration. FIG. 1 reproduces the five main components of the lens homogenate obtained by means of FPLC filtration and those of the molecular weights allocated according to the retention time. The peak area obtained after 15 min. exposure without riboflavin serves as reference parameter (=100%).

Reagents used:

Lens homogenate 5.74±0.13 mg/ml
Riboflavin 25 um
Dihydrolipoate 0.05–1.00 mM

The batch volume was 2.00 ml; reaction temperature 37° C; reaction time t=15 min; light intensity 30 klux (4 nitrophot bulbs of 500 W each)

B. Exposure of bovine eye lens extract (lens homogenate LH) and determination of the oxidation of free thiol groups in the lens homogenate 1. Determination of free protein sulfydryl groups This test is based on a method after ELLMAN (1958, 1959) and covers the LH groups available in solution.

Free SH-groups reductively release the strongly yellow-dyed chromogen 2-nitro-5-mercaptobenzoate from colourless, disulfidic Ellman's reagent DTNB (5,5'-dithio-bis-2-nitrobenzoic acid, dissolved in methanol) (SEKLAK & LINDSAY, 1968). In so doing, the extinction of this dyestuff at 412 nm correlates linearly with the SH concentration used in the range of 10–100 uM SH. A typical assay is composed as follows:

| | | |
|---|---|---|
| Phosphate buffer pH 7.4 | 100 mM | (1.00 ml 0.2 M) |
| Test solution | 10–100 um SH | (0.20 ml 0.1–1 mM SH) |
| aqua dest | ad 2.00 ml | |
| DTNB | 200 uM | (0. 20 ml 2 mM DTNB in methanol) |

The determination reaction is started by adding DTNB and the dyestuff formed is determined photometrically ($E_{412nm}$) after 30 min at room temperature.

2. Oxidation of free thiol groups in the lens homogenate

Lens proteins have a comparatively high concentration of free SH-groups. If lens proteins are exposed to oxidative stress, the SH group decrease can serve as an indication of the extent of the damage caused. It is examined whether dihydrolipoic acid can intervene in the oxidation processes. Exposed riboflavin serves as oxidative system. The quantitative recording of the SH-groups occurs using the modified method after Ellman.

Fresh lens homogenate has an SH concentration of 2.25±0.12 mM which decreases steadily, despite storage at −20° C. and coating with nitrogen. Thus, 1.93±0.05 mM SH are still detectable in the lens homogenate after 8 weeks' storage, representing a loss of some 14%. The SH-decrease occurs much more quickly at room temperature: after 24 hours about 5–10% have already oxidised after 24 hours. If the SH concentration is related to the protein content of the lens homogenate, the following absolute values are obtained:

Lens homogenate fresh: 19.60±1.05 umol SH/g protein

Lens homogenate (8 weeks at −20° C.): 16.83±0.44 umol SH/g protein

This test examined to what extent the SH concentration of the photooxidised lens homogenate changes in this test system and examined the effect of the dihydrolipoic acid on this indicator. After 30 min reaction time the dyestuff is quantified at 412 nm. Since riboflavin even absorbs in this range, 0.50 ml from the incubation batch is used as reference in the Ellman test without DTNB. Use of this type of reference also takes into account the fact that riboflavin even oxidizes in the light, as expressed in an increasing bleaching of the solution.

In this batch, dihydrolipoic acid impaired determination of the lens homogenate-SH since this was above all present in the batch above all in higher concentrations still above 50 uM after 15 min. exposure with riboflavin, i.e. the $E_{412nm}$ values were outside the measuring range and it was mainly dihydrolipoic acid that way measured and not lens homogenate-SH. To be able to nevertheless measure the influence on the SH-groups of the lens homogenate, the batches were gel-filtered through NAP™-25 columns after incubation in the light, whereby the dihydrolipoic acid was separated from the lens proteins. The approximately dihydrolipoic acid-free fraction was now used in the Ellman-determination and the sulfhydryl content determined. The NAP™-25 columns separate in the range of 1 to 5 dkal, i.e. proteins with a molecular weight of over 5 kdal are eluted with the elution agent. The result, however, is also that the glutathion of the lens homogenate and small SH-containing peptides are separated as well. In addition, the samples are diluted by the gel filtration, although this is balanced by a higher sample aliquot in the Ellman batch. Dihydrolipoic acid inhibits SH-group oxidation of the lens proteins in dependence of concentration.

Figure 2:
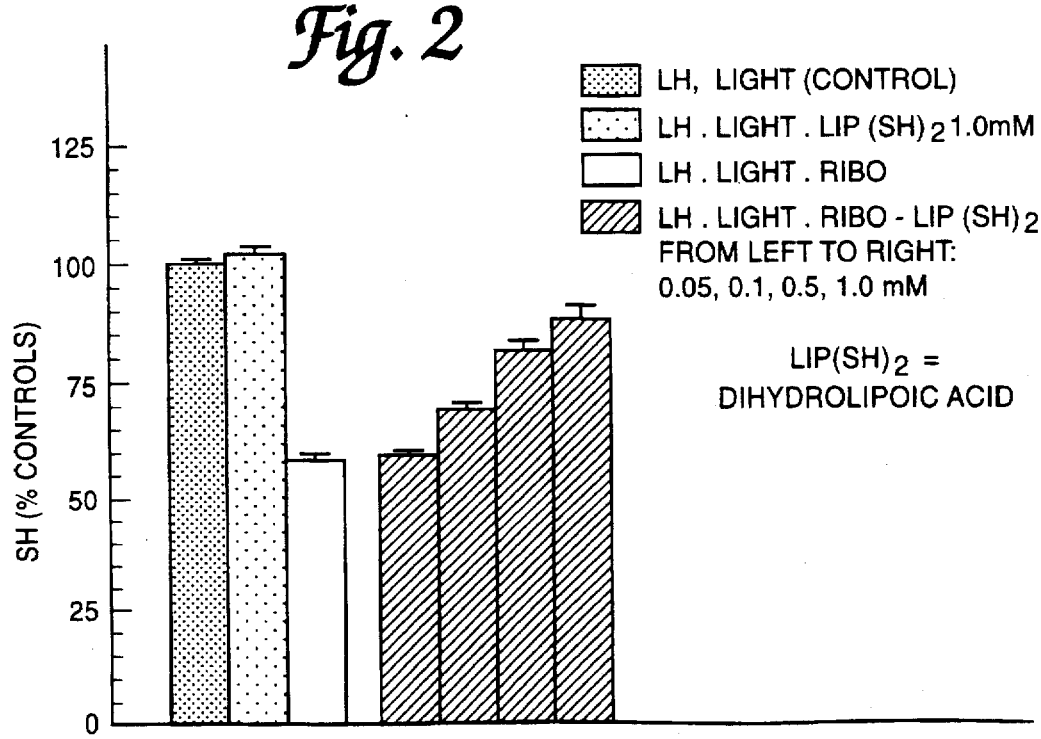
FIG. 2 shows results of an oxidation of SH-groups in a lens homogenate by exposed riboflavin and the influence of dihydrolipoic acid.

FIG. 2 shows these results of the oxidation of SH-groups in the lens homogenate by exposed riboflavin and the influence of dihydrolipoic acid.

The SH-loss of the control resulting from gel filtration is 7.1±0.4 mM (approx. 15%). Comparing the protein contents before and after gel filtration, a loss of 0.52±0.06 mg/ml (approx. 18%) is found. If the elution of a standard protein from the NAP™-25 column is checked, a yield of 98.5±3.4% is obtained in the 3.5 ml eluate. This means, however, that the loss of SH or protein of the gel filtered lens homogenate is provoked by separated low molecular components.

For use according to the invention, dihydrolipoic acid or its physiologically acceptable salts are formulated to administrable medicaments together with conventional auxiliary substances, it also being possible to use the salt formers in excess, i.e. in an amount higher than equimolar.

For salt formation it is possible to use conventional bases or cations which are physiologically acceptable in the salt form. Examples hereof are: acceptable alkaline or alkaline earth metals, ammonium hydroxide, basic amino acids such as arginin and lysin, amines of the formula $NR_1R_2R_3$ where the radicals $R_1$, $R_2$ and $R_3$ are the same or different and represent hydrogen, $C_1$–$C_4$-alkyl or $C_1$–$C_4$ oxyalkyl such as mono- and diethanolamine, 1-amino-2-propanol, 3-amino-1-propanol; alkylenediamine with one alkylene chain of 2–6 carbon atoms as well as ethylene diamine or hexamethylene tetramine, saturated cyclic amino compounds with 4–6 ring carbon atoms such as piperidine, piperazine, pyrrolidine, morpholine; N-methylglucamin, creatine, trometamol.

Dihydrolipoic acid as a pharmaceutical composition may be applied to the skin or mucous membrane or to the inside of the body, for example oral, enteral, pulmonal, nasal, lingual, intravenous, intra-arterial, intracardial, intramuscular, intraperitoneal, intracutaneous, subcutaneous and in the vitreous body or the anterior eye chamber.

Apart from the systemic, oral or parenteral (i.v., i.m., i.c. and s.c.) application of dihydrolipoic acid, the topical application of dihydrolipoic acid solutions, suspension, emulsions and gels may also be corneally and conjunctivally. In addition, applications of the substances is also possible by means of release via a medicament reservoir localised in the conjunctival sac or subconjuctival, dermal, subdermal, intraocular, articular or in other body tissue.

Application may also be by giving the substances in sustained release and also non-sustained release form to endoprostheses and implants.

Other antioxidants that may for example be used are sodium sulfite, sodium hydrogen sulfite, sodium metabisulfite, ascorbic acid, ascorbyl palmirate, -myristate, -stearate, gallic acid, gallic acid alkyl ester, butylhydroxyanisol, nordihydroguaiaretic acid, tocopherols and synergists (substances that bind heavy metals by complex formation, for example lecithin, ascorbic acid, phosphoric acid, ethylene diaminotetraacetic acid, citrates, tartrates). Addition of the synergists substantially increases the antioxygenic effect of the antioxidants. Conserving agents that may for example also be used are sorbic acid, p-hydroxybenzoic acid esters (for example lower alkyl esters), benzoic acid, sodium benzoate, trichlorisobutyl alcohol, phenol, creosol, benzethonium chloride, chlorohexidine and formalin derivatives.

It is also possible to use polyphenols as additives. Rutin, quercetin and morin or mixtures thereof are particularly suitable.

It is in some cases also appropriate to add preservatives, stabilisers, buffers, masking flavors, sweeteners, dyestuffs, antioxidants and complex formers and the like. Complex formers that may for example be used are: chelate formers such as ethylene diamino tetraacetic acid, nitrilotriacetic acid, diethylene triamine pentascetic acid as well as salts thereof.

The complex formers may also be those which contain dihydrolipoic acid in an interstice. Examples hereof are urea, thiourea, cyclodextrins, amylose.

To stabilize the active substance molecule the pharmaceutical composition is preferably adjusted to a pH range of approx. 6–9 with physiologically acceptable bases or buffers. In general as neutral or weakly basic (up to pH 8) a pH value as possible is preferred.

In the case of parenteral formulations these are in particular sterile an or sterilized formulations.

Examples of carriers and auxiliary substances are gelatins, natural sugars such as cane sugar or lactose, lecithin, pectin, starch (e.g. corn starch or amylose), cyclodextrins and cyclodextrin derivatives, dextran, polyvinylpyrrolidone, polyvinyl acetate, gum arabic, alginic acid, tylose, lycopodium, silicic acid (e.g. colloidal), cellulose, cellulose derivatives (e.g. cellulose ethers in which the cellulose hydroxy groups are partially etherified with lower saturated aliphatic alcohols and/or lower saturated aliphatic oxyalcohols, e.g., methyloxypropyl cellulose, methyl cellulose, hydroxypropyl methyl cellulose, hydroxypropyl methyl cellulose phthalate); fatty acids as well as magnesium, calcium or aluminium salts of fatty acids with 12–22 carbon atoms, in particular saturated (e.g. stearates), emulsifiers, oils and fats, in particular vegetable (e.g. peanut oil, castor oil, olive oil, sesame oil, cottonseed oil, corn oil, wheat germ oil, sunflower seed oil, cod liver oil, in each case also hydrated); glycerol esters and polyglycerol esters of saturated fatty acids $C_{12}H_{24}O_2$ to $C_{18}H_{36}O_2$ and mixtures thereof, where the glycerol hydroxy groups are totally or also only partially esterified (e.g. mono-, di- and triglycerides); pharmaceutically acceptable mono- or multivalent alcohols and polyglycols such as polyethylene glycols (molecular weight range for example 300 to 1500) as well as derivatives thereof, polyethylene oxide, esters of aliphatic saturated or unsaturated fatty acids (2–22 carbon atoms, in particular 10–18 carbon atoms) with monovalent aliphatic alcohols (1–20 carbon atoms) or multivalent alcohols such as glycols, glycerol, diethylene glycol, pentaerythrit, sorbitol, mannitol, etc., which may optionally also be etherified, esters of citric acid with primary alcohols, acetic acid, urea, benzyl benzoate, dioxolans, glycerol formals, tetrahyxdrofurfuryl alcohol, polyglycol ethers with $C_1$–$C_{12}$ alcohols, dimethylacetamide, lactamides, lactates, ethyl carbonates, silicons (in particular medium-viscous polydimethylsiloxans), calcium carbonate, sodium carbonate, calcium phosphate, sodium phosphate, magnesium carbonate and the like.

Other auxiliary substances that may be used are those which effect the disintegration of solid formulations (so-called disintegrants) such as: cross-linked polyvinylpyrrolidone, sodium carboxymethyl starch, sodium carboxymethyl cellulose or microcrystalline cellulose. It is also possible to use known casing substances such as polymerisates as well as copolymerisates of acrylic acid and/or methacrylic acid and/or esters thereof; copolymerisates of acrylic and methacrylic acid esters with a low ammonium group content (e.g. Eudragit® RS), copolymerisates of acrylic and methacrylic acid esters and trimethyl ammonium methacrylate (e.g. Eudragit® RL); polyvinylacetate; fats, oils, waxes, fatty alcohols, hydroxypropyl methyl cellulose phthalate or -acetate succinate; cellulose acetate phthalate, starch acetate phthalate as well as polyvinyl acetate phthalate; carboxymethyl cellulose; methyl cellulose phthalate, methyl cellulose succinate, - phthalate succinate as well as methyl cellulose-phthalic acid half ester; zein; ethyl cellulose as well as ethyl cellulose succinate; shellac, gluten; ethyl carboxyethyl cellulose; ethacrylate-maleic acid anhydride copolymer; styrol-maleic acid copolymerisate; 2-ethylhexyl-acrylate maleic acid anhydride; crotonic acid-vinyl acetate copolymer; glutaminic acid/glutaminic acid ester copolymer; carboxymethyl ethyl-cellulose glycerol monooctanoate; cellulose acetate succinate; polyarginin.

Plasticising agents for casing substances that may be used are:

Citrin and tartaric acid esters (acetyl triethyl citrate, acetyl tributyl-, tributyl-, triethyl citrate); glycerol and glycerol esters (glycerol diacetate, -triacetate, acetylated monoglycerides, castor oil); phthalic esters (dibutyl-, diamyl-, diethyl-, dimethyl-, dipropylphthalate), di-(2-methoxy- or 2-ethoxyethyl)-phtalate, ethylphthalyl glycolate, butylphthalyl ethylglycolate and butylglycolate; alcohols (propylene glycol, polyethylene glycol of various chain lengths), adipates (diethyladipate, di-(2-methoxy or 2-ethoxyethyl)-adipate); benzophenon; diethyl- and dibutyl sebacate, dibutyl succinate, dibutyltartrate; diethylene glycol dipropionate; ethylene glycol diacetate, -dibutyrate, -dipropionate; tributyl phosphate, tributyrin; polyethylene glycol sorbitan monooleate (polysorbates such as polysorbate 80); sorbitan monooleate.

To prepare solutions or suspensions it is for example possible to use water or physiologically acceptable organic solvents, such as for example alcohols (ethanol, propanol, isopropanol, 1,2-propylene glycol, polyglycols and derivatives thereof, fatty alcohols, partial esters of glycerol), oils (for example silicon oil, peanut oil, olive oil, sesame oil, almond oil, sunflower oil, soya bean oil, castor oil, cattle hoof oil), paraffins, dimethyl sulfoxide, triglycerides and the like).

For injectable solutions or suspensions it is for example possible to use non-toxic parenterally acceptable diluents or solvents, such as for example: water, 1,3-butane diol, ethanol, 1,2-propylene glycol, polyglycols mixed with water, glycerol, Ringer's solution, isotonic salt solution or also solidified oils including synthetic mono- or diglycerides or fatty acids such as oleic acid.

For the preparation of the formulations it is possible to use known and conventional solubilisers or emulsifiers. Solubilisers and emulsifiers that may for example be used are: polyvinyl pyrrolidone, sorbitan fatty acid esters such as sorbitan trioleate, phosphatids such as lecithin, acacia, tragacanth, polyoxyethylated sorbitan monooleate and other ethoxylated fatty acid esters of sorbitan, polyoxyethylated fats, polyoxyethylated oleotriglycerides, linolisated oleotriglycerides, polyethylene oxide condensation products of fatty alcohols, alkylphenolen or fatty acids or also 1-methyl-1-(2-hydroxyethyl)imidazolidon-(2). Polyoxylethylated in this context means that the appropriate substances contain polyoxyethylene chains, the degree of polymerisation of which generally lies between 2 to 40 and in particular between 10 to 20. Polyoxyethylated substances of this kind may for example be obtained by reaction of hydroxyl group-containing compounds (for example mono- or diglycerides or unsaturated compounds such as those which contain oleic acid radicals) with ethylene oxide (e.g. 40 Mol ethylene oxide per 1 Mol glyceride).

Examples of oleotriglycerides are olive oil, peanut oily castor oil, sesame oil, cottonseed oil, corn oil.

The daily doses in the use according to the invention are 0.01 to 800 mg, preferably 0.1 to 600 mg and in particular 0.2 to 200 mg dihydrolipoic acid in the form of the racemate.

The maximum daily dosage should not exceed 800 mg. The daily doses may be used in the form of a single administration of the entire amount or in the form of 1 to 6, in particular 1 to 4 partial doses per day. In general, administration of from 1 to 4 times, in particular 1 to 3 times daily is preferred. The preferred daily dose for the dihydrolipoic acid is for example 80 mg for the parenteral form of application and 200 mg for the oral form. In particular the daily dose for the parenteral application form is 50 mg and 150 mg for the oral form.

Use may also be as a systemic (oral, parenteral), administered medicament.

Dihydrolipoic acid may in particular also be applied in the form of a solution, for example peroral, topical, parenteral (intravenous, intra-articular, intramuscular, subcutaneous), inhalative, rectal, transdermal or vaginal, in the vitreous body of the eye, intra-ocular in the anterior eye chamber, or in the conjunctival sac of the eye.

Medicaments containing dihydrolipoic acid as active substance may, for example, be formulated in the form of tablets, capsules, pills or coated tablets, granulates, suppositories, pellets, plasters, solutions or emulsions, the active substance being combined with appropriate auxiliary substances and carriers. In the case of solutions, these contain for example 0.5 to 20% by weight, preferably 1 to 10% by weight of dihydrolipoic acid.

The dosage unit of the medicament containing dihydrolipoic acid or a therapeutically applicable salt thereof may, for example, contain:

a) in the case of peroral medicinal forms: 10 to 800 mg, preferably 20 to 600 mg, in particular 20 to 200 mg dihydrolipoic acid. The doses may for example be given 1 to 6, preferably 1 to 4, in particular 1 to 3 times daily. A total dose of 800 mg per day should, however, not be exceeded. The same applies to the following medicinal forms listed under b) to e).

b) in the case of parenteral medicinal forms (e.g. intra-ocular or intravenous, intramuscular or intra-articular): 0.01 to 300 mg, preferably 0.15 to 200 mg, in particular 1 to 100 mg dihydrolipoic acid. The doses may for example be given 1 to 6, preferably 1 to 4, in particular 1 to 3 times daily.

c) in the case of medicinal forms for rectal or vaginal application: 10 to 500 mg, preferably 20 to 400, in particular 30 to 200 mg dihydrolipoic acid. The doses may for example be given 1 to 6, preferably 1 to 4, in particular 1 to 3 times daily.

d) in the case of medicinal forms for application to the skin and mucous membranes, conjunctival sac or intra-ocular (e.g. as solutions, lotions, emulsions, ointments, plasters, etc.): 0.01 to 800 mg dihydrolipoic acid, preferably 0.1 to 250 mg, in particular 0.2 to 200 mg dihydrolipoic acid. The doses may for example be given 1 to 6, preferably 1 to 4, in particular 1 to 3 times daily.

It is of course also possible to prepare galenic formulations which contain the above dosage units 2 to for example 10 times. In particular capsules contains 20 to 600 mg, pellets or granulates 20 to 400 mg, suppositories 20 to 300 mg dihydrolipoic acid.

The above-cited weight amounts refer in each case to pure dihydrolipoic acid, i.e. not to the salts. If salts are used, the dose amounts must correspond in each case and be appropriately increased according to the changed molecular weight.

It is for example possible to use for oral application:

1) Dihydrolipoic acid or a pharmaceutically acceptable salt of dihydrolipoic acid, together with conventional carriers and/or diluents and/or auxiliary substances mixed and/or homogenised and optionally cast the mixture so obtained into hollow cells of appropriate size or fill into capsules of appropriate size or granulate and then optionally press into tablets with the addition of other conventional auxiliary substances or fill into capsules containing in the dosage unit 0.01 to 800 mg dihydrolipoic acid or a pharmaceutically acceptable salt of dihydrolipoic acid. The preparation of this formulation occurs at temperatures between 0° and 120° C., preferably 20° to 80° C.

2) Dihydrolipoic acid or a pharmaceutically acceptable salt of dihydrolipoic acid, optionally with an antioxidant as well as optionally one or several of the following substances: starch, cyclodextrin, urea, cellulose, lactose, formalin-casein, modified starch, magnesium stearate, calcium hydrogen phosphate, silicic acid, optionally granulates the mixture obtained with an aqueous solution which contains as constituent at least gelatin, starch, polyvinyl pyrrolidone, vinyl pyrrolidone-vinyl acetate copolymerisate and/or polyoxyethylene sorbitan monooleate, optionally homogenises the granulate with one or several of the above-mentioned auxiliary substances, and presses this mixture into tablets or fills it into capsules, the tablets or capsules containing in the dosage unit in each case 0.01 to 800 mg active substance dihydrolipoic acid or a salt thereof. This formulation is prepared at temperatures between 0° and 120° C., preferably 20° to 80° C.

For topical application it is for example possible to use:

1) Dihydrolipoic acid or a pharmaceutically acceptable salt of dihydrolipoic acid, optionally with 0.001 to 1 part by weight (related to 1 part by weight of dihydrolipoic acid) antioxidant as well as optionally with addition of one or several emulsifiers and/or complex formers with at least one of the following substances to a mixture containing 0.5 to 20 percent by weight of dihydrolipoic acid, homogenized and optionally emulsified: water, glycerin, paraffin, Vaseline, aliphatic alcohol with 12 to 25 carbon atoms, aliphatic monocarboxylic acid with 15 to 20 carbon atoms, sorbitan monopalmitate, polyoxyethylene polyol fatty acid ester, mono- or multivalent lower molecular aliphatic alcohol, fatty acid glyceride, wax, silicon, polyethylene glycol, polyethylene oxide. This formulation is prepared at temperatures between 20° and 120° C.

It is of course possible to add polyphenols such as rutin, quercitin or morin or mixtures thereof or a pharmaceutically applicable salt.

2) Dihydrolipoic acid or a pharmaceutically acceptable salt of dihydrolipoic acid optionally with 0.001 to 1 part by weight (related to 1 part by weight of dihydrolipoic acid) antioxidant as well as optionally with addition of a complex former and/or an emulsifier water, physiologically acceptable alcohols, dimethyl sulfoxide, polyethylene glycol or oils or mixtures thereof and optionally fills the solution so-obtained with as much water, alcohol, dimethyl sulfoxide, polyethylene glycol or oil so that the final solution, final suspension or final emulsion contains 0–5–20 percent by weight of active substance dihydrolipoic acid. This formation is prepared at temperatures between 30° and 100° C. It is of course possible to add polyphenols such as rutin, quercetin or morin or mixtures thereof or a pharmaceutically acceptable salt.

3) Cream containing 10% dihydrolipoic acid 50 g polyoxyethylene-40-stearate (trade name.: Myrj®52), 80 g cetyl stearyl alcohol, 200 g white Vaseline, 50 g viscous paraffin and 5 g dimethicone are melted together in a homogenising apparatus. 1.26 g methyl-4-hydroxybenzoate and 0.533 g propyl-4-hydroxybenzoate are dissolved in the melt.

1.4 g methyl-4-hydroxybenzoate and 0.6 g propyl-4-hydroxybenzoate are dissolved in 511.207 g purified water at 70° C. The solution is emulsified into the above-obtained fat melt. The emulsion is homogenised and cooled to room temperature with stirring. 100 g dihydrolipoic acid are then stirred into the cream and homogenised again in a vacuum.

4) Eye drops with 0.01 to 25 mmol dihydrolipoic acid as racemate

To prepare eye drops it is preferred to add preservatives, lubricants and effective wetting agents to the preparation.

Preservatives that may for example be used are benzalkonium chlorides which have an antiseptic and surface-active effect. It is also preferred to add glycerin and physiological salt solution to the eye drops.

For 100 ml eye drops

| Dihydrolipoic acid 0.01 to 25 mmol | |
|---|---|
| $H_2NaPO_4.H_2O$ | 0.018 g |
| $HNa_2PO_4.12\ H_2O$ | 0.190 g |
| glycerin and/or dextran | 0.100 g |
| sterile water up to | 100 ml |

Stabilizers, preservatives in adequate amount.

Topical use is effected dropwise directly into the eye. The frequency of application varies from once to five times daily. Another mode of use consists in applying the above-described formulation to the eye via a carrier. Suitable carriers are keratin disks or soft contact lenses which are applied after pre-incubation. Alternatively, liposome preparations may also be added to the eye drops for direct application or application via a carrier.

I claim:

1. A method of suppressing or reducing an intolerance reaction resulting from an implant or endoprosthesis comprising contacting an area of living tissue in contact with or near the implant or endoprosthesis with an effective amount of a pharmaceutical composition comprising dihydrolipoic acid, or a physiologically acceptable salt of dihydrolipoic acid, or mixture thereof such that the intolerance reaction is suppressed or reduced.

2. The method according to claim 1 wherein the intolerance reaction is associated with a region of or near an eye.

3. The method according to claim 1 wherein the implant is an ophthalmological implant.

4. The method according to claim 1 wherein the area of living tissue is contacted with the pharmaceutical composition before the intolerance reaction develops.

5. The method according to claim 1 wherein the pharmaceutical composition comprises a racemic mixture of R- or S-dihydrolipoic acid.

6. The method according to claim 1 wherein the pharmaceutical composition comprises an enantiomerically pure form of dihydrolipoic acid.

7. The method according to claim 1 wherein the pharmaceutical composition further comprises polyphenol.

8. The method according to claim 7 wherein the polyphenol is selected from the group consisting of rutin, quercetin, morin, and mixtures thereof.

* * * * *